US00PP30119P2

(12) United States Plant Patent
Trees

(10) Patent No.: US PP30,119 P2
(45) Date of Patent: Jan. 15, 2019

(54) ***SCABIOSA* PLANT NAMED 'BALFLUTTURITE'**

(50) Latin Name: *Scabiosa columbaria*
Varietal Denomination: Balflutturite

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 8 days.

(21) Appl. No.: 15/731,885

(22) Filed: Aug. 18, 2017

(51) Int. Cl.
*A01H 5/02* (2018.01)

(52) U.S. Cl.
USPC ..... Plt./478
CPC ..... *A01H 5/02* (2013.01)

(58) Field of Classification Search
USPC ..... Plt./478
See application file for complete search history.

*Primary Examiner* — Anne Marie Grunberg
(74) *Attorney, Agent, or Firm* — Audrey Charles

(57) ABSTRACT

A new and distinct cultivar of *Scabiosa* plant named 'Balflutturite', characterized by its white-colored flowers, medium green-colored foliage, and moderately vigorous, compact-mounded growth habit, is disclosed.

1 Drawing Sheet

Latin name of genus and species of plant claimed: *Scabiosa columbaria.*

Variety denomination: 'Balflutturite'.

BACKGROUND OF THE INVENTION

The present invention relates to a new and distinct cultivar of *Scabiosa* plant botanically known as *Scabiosa columbaria* and hereinafter referred to by the cultivar name 'Balflutturite'.

The new cultivar originated in a controlled breeding program in Guadalupe, Calif. during October 2013. The objective of the breeding program was the development of *Scabiosa* cultivars that have large inflorescences with rich flower colors and a compact growth habit.

The new *Scabiosa* cultivar is the result of open-pollination. The female (seed) parent of the new cultivar is the proprietary *Scabiosa columbaria* breeding selection coded SCB-327, not patented, characterized by its white-colored flowers, dark green-colored foliage, and vigorous, mounded growth habit. The male (pollen) parent of the new cultivar is unknown. The new cultivar was discovered and selected as a single flowering plant within the progeny of the above stated open-pollination during August 2014 in a controlled environment in Guadalupe, Calif.

Asexual reproduction of the new cultivar by terminal stem cuttings since August 2014 in Guadalupe, Calif., and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balflutturite' as a new and distinct cultivar of *Scabiosa* plant:

1. White-colored flowers;
2. Medium green-colored foliage; and
3. Moderately vigorous, compact-mounded growth habit.

Plants of the new cultivar differ from plants of the female parent primarily in having a more compact growth habit.

Of the many commercially available *Scabiosa* cultivars, the most similar in comparison to the new cultivar is Flutter Rose Pink 'Balfluttropi', U.S. Plant Pat. No. 27,809. However, in side-by-side comparison, plants of the new cultivar differ from plants of 'Balfluttropi' in at least the following characteristics:

1. Plants of the new cultivar have a flower color that is different from plants of 'Balfluttropi';
2. Plants of the new cultivar have a lighter foliage color than plants of 'Balfluttropi'; and
3. Plants of the new cultivar have smaller diameter inflorescences than plants of 'Balfluttropi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balflutturite'. The plants were approximately six months old. Plants were grown in one-gallon containers for approximately five weeks in a greenhouse and 14 weeks outdoors in Elburn, Ill. Plants were given two pinches, one before transplant and one at transplant.

DETAILED BOTANICAL DESCRIPTION

Figure 1:
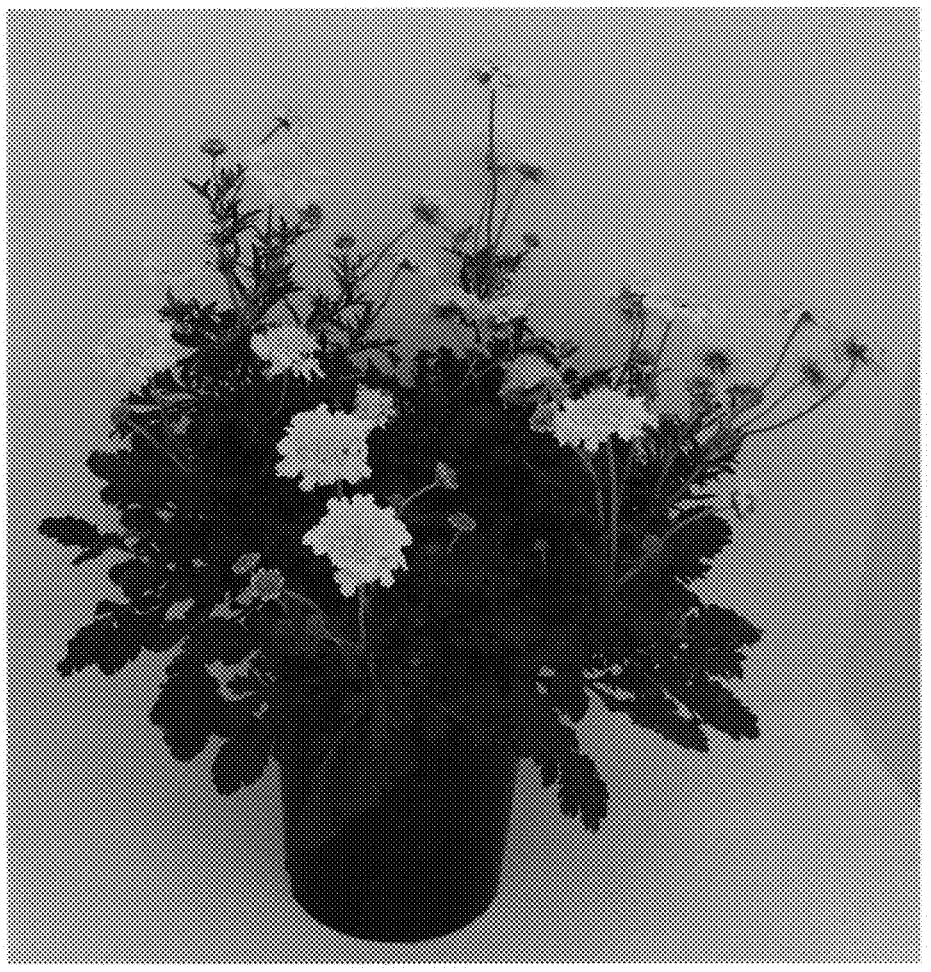
FIG. 1 illustrates a side view of the overall growth and flowering habit of 'Balflutturite'.
Figure 2:
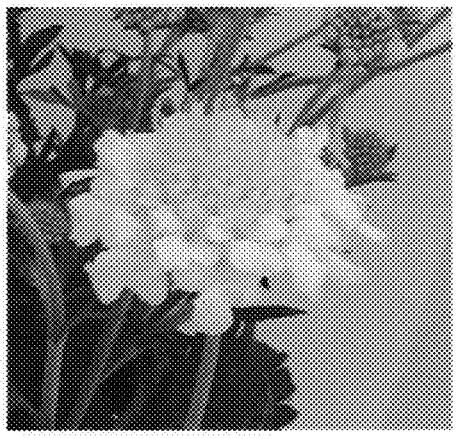
FIG. 2 illustrates a close-up view of an individual inflorescence of 'Balflutturite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2017 under natural light conditions in West Chicago, Ill.

The following descriptions and measurements describe approximately six-month old plants produced from cuttings from stock plants and grown under conditions comparable to those used in commercial practice. The plants were grown in one-gallon containers for approximately five weeks in a greenhouse and 14 weeks outdoors in Elburn, Ill. Plants were given two pinches, one before transplant and one at transplant. Greenhouse temperatures were maintained at approximately 60° F. to 68° F. (15.5° C. to 20° C.) during the day and approximately 55° F. to 60° F. (13° C. to 15.5° C.) during the night. No supplemental lighting was provided. Measurements and numerical values represent averages of typical plants.

Botanical classification: *Scabiosa columbaria* 'Balflutturite'.

Parentage:

*Female parent.*—Proprietary *Scabiosa columbaria* breeding selection coded SCB-327, not patented.

*Male parent.*—Unknown.

Propagation:

*Type cutting.*—Terminal stem.

*Time to initiate roots.*—Approximately 10 to 12 days.

*Time to produce a rooted cutting.*—Approximately 35 to 42 days.

*Root description.*—Fibrous, fine to medium, creamy white to light brown in color.

*Rooting habit.*—Freely branching, medium density.

Plant description:

*Commercial crop time.*—Approximately 8 to 10 weeks from a rooted cutting to finish in a 10 cm pot.

*Growth habit and general appearance.*—Moderately vigorous, compact-mounded.

*Hardiness.*—USDA Zone 5a (−20° F. to −15° F./−28.9° C. to −26° C.).

*Size.*—Height from soil level to top of plant plane: Approximately 34.0 cm. Width: Approximately 40.0 cm.

*Branching habit.*—Basal rosette, freely branching, pinching enhances basal branching. Quantity of main stems per plant: Approximately 5, with each main branch having 4 to 6 lateral branches.

*Main stems.*—Strength: Strong. Length to base of peduncle: Approximately 16.0 cm. Diameter: Approximately 5.0 mm to 7.0 mm. Length of central internode: Approximately 3.0 mm. Texture: Densely pubescent with appressed hairs. Color of young and mature stems: Close to 138A, appears lighter due to pubescence.

Foliage description:

*General description.*—Quantity of leaves per main branch: Approximately 13. Fragrance: None detected. Form: Simple. Arrangement: Opposite.

*Leaves.*—Aspect: Acute angle to stem, tips turning downward with age. Shape: Overall narrowly obovate. Margin: Pinnatisect, less dissected earlier in season and as a young plant. Apex: Acute to acuminate. Base: Attenuate, sessile. Venation pattern: Pinnate. Length of mature leaf: Approximately 14.0 cm. Width of mature leaf: Approximately 5.0 cm. Texture of upper and lower surfaces: Densely pubescent. Color of upper surface of young and mature foliage: 137A to 137B with venation indistinguishable from leaf lamina except for midvein of 145C. Color of lower surface of young and mature foliage: 137B with venation of 146D.

Flowering description:

*Flowering habit.*—'Balflutturite' is freely flowering under outdoor growing conditions with substantially continuous blooming from late spring through late summer.

*Lastingness of individual inflorescence on the plant.*—Approximately 8 to 10 days.

Inflorescence description:

*General description.*—Type: Involucrate heads. Corolla not persistent, bristled calyx persistent. Shape: Dome. Aspect: Facing upward to slightly outward. Arrangement: Terminal involucrate heads displayed above the foliar plane on long peduncles. Fragrance: None detected. Quantity per plant: Approximately 27, with an additional 19 senesced inflorescences removed for photograph. Diameter: Approximately 4.8 cm. Inner cushion diameter: Approximately 2.7 cm. Depth: Approximately 2.0 cm.

*Peduncle.*—Strength: Strong. Aspect: Erect to slightly wiry. Length: Approximately 6.0 cm to 15.0 cm. Diameter: Approximately 2.0 mm. Texture: Densely pubescent with appressed hairs. Color: Close to 138A, appears lighter due to pubescence.

*Inflorescence bud.*—Rate of opening: Generally takes 2 to 4 days for bud to progress from first color to fully open flower.

*Bud just before opening.*—Shape: Obovate. Length: Approximately 7.0 mm. Diameter: Approximately 3.0 mm. Texture: Densely pubescent. Color: 145D with NN155D at apex.

*Outer florets.*—Quantity per inflorescence: Approximately 23. Arrangement: In two whorls. Shape: Funnel, 5 lobes, 3 broad upper lobes with the central lobe being the largest, and 2 small lower lobes. Lobes are fused at the base forming a tube. Length of outer floret: Approximately 2.0 cm. Width of outer floret: Approximately 1.4 cm. Shape of all lobes: Obovate to oblong. Margin of all lobes: Scalloped, slightly wavy. Apex of all lobes: Rounded. Length of central lobe from throat: Approximately 1.0 cm. Width of central lobe: Approximately 7.0 mm. Length of lateral lobes from throat: Approximately 8.0 mm. Width of lateral lobes: Approximately 6.0 mm. Length of lower lobes from throat: Approximately 4.0 mm. Width of lower lobes: Approximately 4.0 mm. Texture of upper surface of all lobes: Glabrous. Texture of lower surface of all lobes: Central lobe and base of other lobes densely pubescent. Color of upper surface of all lobes when fully open: NN155D. Color of lower surface of all lobes when fully open: NN155D. Tube: Length: Approximately 1.0 cm. Diameter at base: Approximately 1.0 mm. Diameter at throat: Approximately 2.0 mm. Texture of inner surface: Sparsely pubescent. Texture of outer surface: Densely pubescent. Color of inner and outer surfaces: NN155D.

*Inner florets.*—Quantity per inflorescence: Approximately 53. Arrangement: In multiple whorls. Shape: Funnel, 5 lobes, 3 broad upper lobes with the central lobe being the largest, and 2 small lower lobes. Lobes are fused at the base forming a tube. Length of inner floret: Approximately 1.3 cm. Width of inner floret: Approximately 5.0 mm. Shape of all lobes: Oblong with lower lobes orbicular. Margin of all lobes: Entire, slightly wavy. Apex of all lobes: Rounded. Length of central lobe from throat: Approximately 6.0 mm. Width of central lobe: Approximately 2.0 mm. Length of lateral lobes from throat: Approximately 4.0 mm. Width of lateral lobes: Approximately 2.0 mm. Length of lower lobes from throat: Approximately 2.0 mm. Width of lower lobes: Approximately 2.0 mm. Texture of upper surface of all lobes: Glabrous. Texture of lower surface of all lobes: Central lobe and lower half of other lobes densely pubescent. Color of upper surface of all lobes when fully open: NN155D. Color of lower surface of all lobes when fully open: NN155D. Tube: Length: Approximately 7.0 mm. Diameter at base: Approximately 1.0 mm. Diameter at throat: Approximately 2.0 mm. Texture of inner surface: Sparsely pubescent. Texture of outer surface: Densely pubescent. Color of inner and outer surfaces: NN155D.

*Calyx.*—Arrangement: 2 whorls. Outer whorl: 5 fused sepals. Shape: Cup-like. Height: Approximately 3.0 mm. Width: Approximately 2.0 mm. Apex: Scalloped. Texture of inner surface: Glabrous. Texture of outer surface: Densely pubescent. Color of inner and outer surfaces: NN155D, translucent with base of 137A. Inner whorl: 5 pappus-like setae attached at base. Length: Approximately 6.0 mm. Color: 145D with tips of 187A and base of 144A.

*Floral bracts.*—Quantity: One per floret. Shape: Obovate. Margin: Entire. Apex: Acute. Base: Attenuate. Length: Approximately 4.0 mm. Width: Approximately 1.0 mm. Texture of inner surface: Glabrous. Texture of outer surface: Densely pubescent. Color of inner and outer surfaces: 137A, outer surface appears lighter due to pubescence.

*Involucral bracts.*—Quantity per inflorescence: Approximately 13. Arrangement: In a single whorl. Shape: Linear to lanceolate. Margin: Entire. Apex: Acute. Base: Truncate. Length: Approximately 8.0 mm. Width: Approximately 2.0 mm. Texture of inner and outer surfaces: Densely pubescent. Color of inner and outer surfaces: 137A, outer surface appears lighter due to pubescence.

*Receptacle.*—Shape: Conical. Height: Approximately 3.0 mm. Diameter: Approximately 3.0 mm. Color: Closest to 145D.

*Reproductive organs.*—Androecium and gynoecium: Present on both inner and outer florets. Stamen quantity: 4 per floret, base of filaments adnate to corolla. Stamen length: Approximately 1.5 cm. Filament length of free portion: Approximately 8.0 mm. Filament color: NN155D. Anther shape: Oblong. Anther length: Approximately 3.0 mm. Anther color: NN155D. Pollen amount: Abundant. Pollen color: NN155A. Pistil quantity: 1 per floret. Pistil length: Approximately 1.0 cm to 1.2 cm. Stigma shape: Flattened. Stigma length: Less than 1 mm. Stigma color: NN155D. Style length: Approximately 9.0 mm to 1.1 cm. Style color: NN155D. Ovary length: Approximately 1.0 mm. Ovary color: NN155D.

Seed and fruit production: Neither seed nor fruit production has been observed.

Disease and pest resistance: Resistance to pathogens and pests common to *Scabiosa* has not been observed.

What is claimed is:

1. A new and distinct cultivar of *Scabiosa* plant named 'Balflutturite', substantially as herein illustrated and described.

* * * * *